US006417220B2

(12) United States Patent
Yoshii et al.

(10) Patent No.: US 6,417,220 B2
(45) Date of Patent: *Jul. 9, 2002

(54) MITOCHONDRIAL MEMBRANE STABILIZER

(75) Inventors: Mitsunobu Yoshii; Shigeo Watabe, both of Tokyo (JP)

(73) Assignee: Daiichi Pharmaceutical Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/269,208
(22) PCT Filed: Sep. 30, 1997
(86) PCT No.: PCT/JP97/03485
§ 371 (c)(1),
(2), (4) Date: May 26, 1999
(87) PCT Pub. No.: WO98/14213
PCT Pub. Date: Apr. 9, 1998

(30) Foreign Application Priority Data

Oct. 1, 1996 (JP) ............................................. 8-260649

(51) Int. Cl.$^7$ ........................ A61K 31/40; A61K 31/44; A61K 31/435
(52) U.S. Cl. ....................... 514/424; 514/258; 514/259; 514/260; 514/291; 514/293; 514/294; 514/307; 514/309; 514/310; 514/311; 514/312; 514/313; 514/314; 514/317; 514/618; 514/619; 514/620; 514/233.2; 514/267
(58) Field of Search ................................ 514/424, 258, 514/233.2, 259, 260, 267, 291, 293, 274, 307, 309, 310, 311, 312, 313, 314, 617, 618, 619, 620

(56) References Cited

U.S. PATENT DOCUMENTS

| 4,341,790 A | * | 7/1982 | Betzing et al. ............. 424/274 |
| 4,385,053 A | | 5/1983 | Reisberg et al. |
| 4,499,094 A | | 2/1985 | Dubroeucq et al. |
| 5,128,338 A | | 7/1992 | Bourguignon et al. |
| 5,886,023 A | * | 3/1999 | Otomo et al. ............... 514/424 |
| 6,107,330 A | * | 8/2000 | Nabeshima et al. ........ 514/424 |

FOREIGN PATENT DOCUMENTS

| EP | 0515866 | 12/1992 |
| JP | 56-2960 | 1/1981 |
| JP | 58201756 | 11/1983 |
| JP | 61280470 | 12/1986 |
| JP | 62-5404 | 2/1987 |
| JP | 2-256617 | 10/1990 |
| JP | 3-46466 | 7/1991 |
| JP | 4-160496 | 6/1992 |
| JP | 4-217682 | 8/1992 |
| JP | 5-163144 | 6/1993 |
| JP | 5-163145 | 6/1993 |
| WO | 95159170 | 7/1995 |

OTHER PUBLICATIONS

English language astract of JP 4–160496, (Feb. 1986).
English language astract of JP 5–163144, (May 1992).
English language astract of JP 5–163145, (Apr. 1987).
English language astract of JP 2–256617, (Dec. 1991).
Choi, D. W. *Trends in Neurosciences*, 11, pp. 465–469 (1998).
Nicotera et al., *Chem. Res. Tozico.*, 3, pp. 484–494 (1990).
Zaiden et al., *J. Neurochem.*, 63, pp. 1812–1819 (1994).
Loew et al., *Proc. Natl. Acad. Sci.*, USA, 91, pp. 12579–12583 (1994).
Kagawa, *Saibo Kogaku* (*Cell technology*), 11, pp 3–11 (1992).
Shigenaga et al., *Proc. Natl. Acad. Sci.*, USA, 91, pp. 10771–10778 (1994).
Tanaka, M., et al., *Naika* (*Medicine*), 77, pp. 881–887 (1996).
Ohnishi, H. et al., *Noshinkei* (*Cerebral Nerve*), 44, pp. 259–264 (1992).
Mitchell, P., *Science*, 206, pp. 1148–1159 (1979).
Mitchell, P., *FEBS Lett.*, 43, pp. 189–194 (1974).
Nakamoto et al., *The 17th Japan Neurology Convention*, Dec. 7–9, (1993).
*Neurosci. Res. Suppl.*, 17, S88. Pp. 2–71 (1992).
Hare, M. F., et al., *JPET*, 266, pp. 1626–1635 (1993).
*TIPS*, Dec., pp. 506–511 (1986).
Luthman et al., "Effects of DM–9384, a pyrrolidone derivative, on ischemia–induced changes in the central monoamine systems", Pharmacology, Biochemistry and Behavior, (Jan. 1992) 41 (1) 231–4.
Bottini et al., "Oxiracetam in dementia: a double–blind, placebo–controlled study", Acta Neurologica Scandinavia, (Sep. 1992) 86 (3) 237–41.
Kinnally et al., "Mitochondrial benzodiazepine receptor linked to inner membrane ion channels by nanomolar actions of ligands", Proc. Natl. Acad. Sci. U.S.A. (1993) 90(4) 1374–8.

* cited by examiner

*Primary Examiner*—Frederick Krass
(74) *Attorney, Agent, or Firm*—Greenblum & Bernstein, P.L.C.

(57) ABSTRACT

A prophylactic and/or therapeutic method for treating a disease caused by mitochondrial functional abnormality, or a disease with mitochondrial functional abnormality, including: administering a prophylactically and/or therapeutically effective amount to a patient in need of such treatment of a medicament including as an active ingredient a substance having a stabilizing effect on mitochondrial membrane by suppressing or eliminating depolarization of mitochondrial membranes which is caused by elevation of intracellular calcium ion concentration, wherein the stabilizing effect on mitochondrial membrane is an action of suppressing or eliminating depolarization of mitochondrial membranes, wherein the depolarization of mitochondrial membranes is caused by elevation of intracellular calcium ion concentration. The disease may be ischemic diseases, toxic diseases, or degenerative diseases. The medicament may be 2-oxo-1-pyrrolidinylacetic acid 2,6-dimethylanilide which acts as a benzodiazepine receptor antagonist.

17 Claims, 10 Drawing Sheets

MITOCHONDRIAL MEMBRANE STABILIZER

This application is a 371 of PCT/JP97/03485, filed Sep. 30, 1997.

TECHNICAL FIELD

The present invention relates to a medicament for prophylactic and/or preventive and/or therapeutic treatment of diseases caused by mitochondrial functional abnormality or diseases with mitochondrial functional abnormality.

BACKGROUND ART

It is known that intracellular calcium ions ($Ca^{+2}$) may become a cytotoxic factor when increased beyond a certain concentration, although they act as an important information transmitter under physiological conditions. In particular, in the nervous system under ischemic conditions, calcium ions flow into cells through the glutamic acid receptor (NMDA type) due to excessive glutamic acid and induce nerve necrosis (Choi, D. W., Trends in Neurosciences, 11, 465–469, 1988). Under healthy conditions, excessive calcium ions are taken into the endoplasmic reticulum and mitochondria when calcium ions flow into cells beyond a certain concentration, and as a result, calcium ion concentrations are homeostatically maintained.

However, when high levels of calcium ions are accumulated in mitochondria for a prolonged period of time and chronic hypoxic conditions are maintained in mitochondria, the mitochondrial energy-generating function (ability to synthesize ATP) becomes degraded, which results in stoppage of various ion pumps present in cellular membranes (Nicotera et al., Chem. Res. Toxico., 3, 484–494, 1990; and Zaiden et al., J. Neurochem., 63, 1812–1819, 1994). In addition, when the state of calcium ion influx is maintained, plasma membranes are depolarized. This may cause disinhibition of NMDA-type glutamate receptor/ion channel complex that is kept in a suppressed condition by magnesium ions, which leads to further acceleration of calcium ion influx as a vicious circle.

If the mitochondrial energy-generating function (ATP synthesis) can be maintained even at the condition of influx and accumulation of a high level of calcium ions in mitochondria, the function of the calcium ion pumps, that are present in plasma membranes, can be kept normal and concentrations of the influxed and accumulated calcium ions in the cells can be lowered. As a result, physiological conditions of the cells may be restored. However, it has been considered that the activation of the mitochondria is substantially impossible under the calcium influx by the reasons set out below.

Energy generation in mitochondria is performed by the process of aerobic glycolysis (TCA cycle). Protons ($H^+$) are produced in the process (electron transfer system), and the generated energy is used to transfer the protons from the inner matrix of mitochondria to the outside.

Extremely high electrochemical potentials are generated across the mitochondrial inner membrane from the outside {1) mitochondrial membrane potentials ($\Psi m$) approximately −150 mV and 2) chemical potentials derived from the difference in proton ($H^+$) concentration across the mitochondrial inner membrane} (Loew et al., Proc. Natl. Acad. Sci., USA, 91, 12579–12583, 1994). The high potential energies based on the active transport of protons ($H^+$) is then used to drive ATP synthesis (Kagawa, Y., Saibo Kogaku (Cell Technology), 11, 3–11, 1992).

However, under physiological conditions, when positively charged calcium ions flow into the mitochondrial matrix, these calcium ions are pumped out by consuming the energy generated by ATPase located in the mitochondrial matrix, so that the mitochondrial membrane potential can be maintained. However, under pathological conditions where ATP activity is degraded, ATPase activity is decreased and the pumping out of calcium ions may become insufficient, so that the potential of the mitochondrial matrix shifts to the positive, thereby reducing $\Psi m$ (decrease of electrical potential).

Under these pathological conditions (a state of depolarized mitochondrial membrane potential), even though the chemical potential generated by the proton ($H^+$) gradient exists, a decrease in the electrochemical potential due to the lowered electrical potential ($\Psi m$) may cause inhibition of the activities of ATP synthase, which finally results in cessation of the mitochondrial ATP synthesis.

It has been suggested that mitochondrial membranes may be depolarized by various exogenous and endogenous factors, and the depolarization may possibly be one cause of mitochondrial functional abnormality. Furthermore, mitochondrial functional abnormality is observed in various diseases, and the abnormality of mitochondrial function is considered as a major cause of some diseases. For example, the abnormality of mitochondrial function is generally recognized in ischemic diseases such as ischemic brain diseases and ischemic heart diseases, Parkinson's disease, Alzheimer's disease, amyotrophic lateral sclerosis (ALS), degenerative diseases due to mitochondrial abnormality such as mitochondrial encephalomyopathy, various toxic diseases such as carbon monoxide poisoning. A substance, which stabilizes mitochondrial membranes by protecting mitochondrial membranes from actions of various exogenous and endogenous factors and maintaining the physiological membrane potential, may be expected to be extremely useful for therapeutic and preventive and prophylactic treatment of these diseases.

DESCRIPTION OF THE INVENTION

An object of the present invention is to provide a substance which has an action of stabilizing mitochondrial membranes by protecting the mitochondrial membranes from actions of various exogenous and endogenous factors, and suppressing or eliminating the depolarization of mitochondrial membranes. Another object of the present invention is to provide a substance having actions of stabilizing mitochondrial membranes, and preventing the abnormality of mitochondrial function with depolarization of mitochondrial membranes. A further object of the present invention is to provide a medicament for prophylactic and/or preventive and/or therapeutic treatment of diseases caused by mitochondrial functional abnormality, or diseases with mitochondrial functional abnormality, which comprises a substance having the aforementioned actions as an active ingredient.

The inventors of the present invention conducted various studies to achieve the foregoing objects, and as a result, they first discovered the existence of a substance which has an action of stabilizing mitochondrial membranes by suppressing or eliminating the depolarization of mitochondrial membranes. The inventors of the present invention conducted further studies and found that, by stabilizing mitochondrial membranes, mitochondrial membranes can be protected from depolarization due to various exogenous and endogenous factors, and/or the physiological polarization condition of mitochondrial membranes can be maintained or restored, thereby physiological energy generation of mitochondria can be maintained or restored. It was also found that a substance having these actions can suppress an action of an agonist, that unstabilizes mitochondrial membrane, by binding as an antagonist to a benzodiazepine receptor present in mitochondrial membranes. The present invention was achieved on the bases of these findings.

The present invention thus provides a medicament for prophylactic and/or preventive and/or therapeutic treatment of a disease caused by mitochondrial functional abnormality, or a disease with mitochondrial functional abnormality, which comprises a substance having stabilizing effect on a mitochondrial membrane as an active ingredient. According to preferred embodiments of the aforementioned medicament of the present invention, there are provided the aforementioned medicament for prophylactic and/or preventive and/or therapeutic treatment wherein the stabilizing effect on the mitochondrial membrane is an action of suppressing or eliminating the depolarization of a mitochondrial membrane; the aforementioned medicament for prophylactic and/or preventive and/or therapeutic treatment wherein the depolarization of the mitochondrial membrane is caused by an elevated intracellular calcium ion concentration; the aforementioned medicament for prophylactic and/or preventive and/or therapeutic treatment wherein the stabilizing effect on mitochondrial membrane is an action of maintaining or restoring ATP producing ability of mitochondria under a physiological state when intracellular calcium ion concentration is elevated; and the aforementioned medicament for prophylactic and/or preventive and/or therapeutic treatment wherein the disease is selected from the group consisting of an ischemic disease, a toxic disease, and a degenerative disease. There is further provided the aforementioned medicament for prophylactic and/or preventive and/or therapeutic treatment wherein the substance is an antagonist for a mitochondrial benzodiazepine receptor.

According to preferred embodiments of the aforementioned medicament of the present invention, there are further provided the aforementioned medicament for prophylactic and/or preventive and/or therapeutic treatment wherein the ischemic disease is an ischemic affection of cranial nerve system or cerebral blood vessel system, ischemic heart disease, renal failure, or hepatic failure; the aforementioned medicament for prophylactic and/or preventive and/or therapeutic treatment wherein the degenerative disease is abnormality of mitochondrial enzyme activity, mitochondrial gene mutation disease, Parkinson's disease, Alzheimer's disease, amyotrophic lateral sclerosis (ALS), mitochondrial encephalomyopathy, or Niemann-Pick's disease; and the aforementioned medicament for prophylactic and/or preventive and/or therapeutic treatment wherein the toxic disease is a gas poisoning, an alcoholic poisoning, a drug poisoning, a pesticide poisoning, a heavy metal poisoning, or a poisoning caused by a toxin derived from a natural animal or a natural plant.

According to another aspect of the present invention, there is provided a method for prophylactic and/or preventive and/or therapeutic treatment of a disease caused by mitochondrial functional abnormality, or a disease with mitochondrial functional abnormality, which comprises administering to a mammal including human an effective amount of a substance having a stabilizing effect on the mitochondrial membrane.

According to further aspects of the present invention, there are provided a mitochondrial membrane stabilizing agent which comprises an antagonist for a mitochondrial benzodiazepine receptor as an active ingredient; and a medicament for prophylactic and/or preventive and/or therapeutic treatment of a disease caused by mitochondrial functional abnormality, or a disease with mitochondrial functional abnormality, which comprises an antagonist for a mitochondrial benzodiazepine receptor as an active ingredient.

BEST MODE FOR CARRYING OUT THE INVENTION

Figure 1:
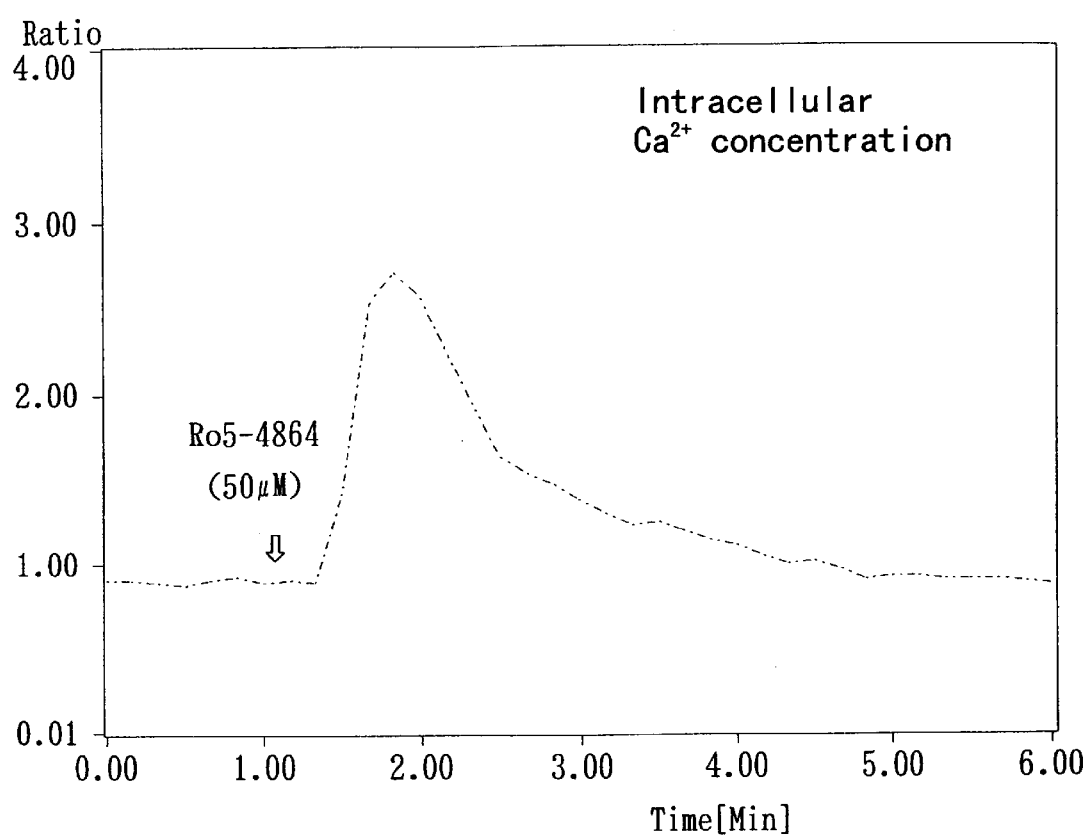
FIG. 1 shows an effect of Ro5-4864, described below, on intracellular $Ca^{2+}$ concentration.

The medicament of the present invention acts on mitochondrial membranes and exhibits a stabilizing effect on the mitochondrial membranes (in particular, mitochondrial inner membranes). As a result, the medicament of the present invention has an action of protecting the mitochondrial membranes from depolarizing effects and the like that are derived from various exogenous factors (exposure to toxic substances and the like) or endogenous factors (abnormality of cellular membrane components due to abnormal expression of genes and the like), and the medicament has an action of maintaining or restoring the physiological state of polarization of mitochondrial membranes and hence maintaining or restoring energy generation at physiological level in mitochondria. In the specification, the term "mitochondrial functional abnormality" is used to mean a concept encompassing any substantial abnormalities of mitochondrial functions including the aforementioned degradation of energy generating ability (hypoactivity). Also in the specification, the term "physiological" means a state substantially the same as conditions in an intracellular environment of a usual cell that maintains normal life supporting actions.

Although no restriction to a specific theory is intended, calcium ion concentration in mitochondria is also increased when intracellular calcium ion concentration is elevated by exogenous or endogenous factors, and this results in reduced ATP generating ability due too depolarization of mitochondrial membranes. The medicament of the present invention has an action of stabilizing mitochondrial membranes, particularly when the intracellular calcium ion concentration is elevated. and the medicament substantially suppresses the depolarization of the membranes completely, or suppresses the depolarization and maintains or restores the physiological ATP producing ability.

In addition, although no restriction to a specific theory is intended, the medicament of the present invention can bind to the mitochondria benzodiazepine receptor (MBR), and acts as a competitive antagonist for an MBR agonist (e.g., 7-chloro-5-(4-chlorophenyl)-1,3-dihydro-1-methyl-2H-1,4-benzodiazepin-2-one: TIPS, December, pp.506–511, 1986) that binds to the receptor and unstabilizes mitochondrial membrane potential. It is considered that the medicament of the present invention stabilizes mitochondrial membranes based on the antagonistic action for MBR, and thus exhibits the aforementioned physiological actions.

The medicament of the present invention is thus characterized by (a) the effect of stabilizing mitochondrial membranes, and based on the aforementioned stabilizing effect, the medicament is characterized in that (b) it protects mitochondrial membranes from depolarizing action deriving from exogenous or endogenous factors, and/or (c) it maintains or restores the physiological polarization of mitochondrial membranes and maintains or restores the physiological energy generation in mitochondria. Therefore, it should be understood that the medicament of the present invention is not limited to a substance having a specific chemical structure, and that any medicament comprising a substance having the aforementioned physiological characteristics falls within the scope of the present invention. Means to verify the aforementioned physiological characteristics will be detailed in the examples in the specification.

Furthermore, the medicament of the present invention comprises an antagonist for the mitochondrial benzodiazepine receptor as an active ingredient, and based on the stabilization of the mitochondrial membrane, the medicament can effectively achieve prophylactic and/or preventive and/or therapeutic treatment of a disease caused by mitochondrial functional abnormality, or with mitochondrial functional abnormality. Means to verify the antagonist action for the mitochondria benzodiazepine receptor will also be specifically explained in the examples in the specification.

Examples of the disease caused by mitochondrial functional abnormality, or the disease with mitochondrial functional abnormality include, for instance, ischemic diseases of organs such as liver, heart, brain, and kidney, and blood vessel system controlling those organs. More specifically, typical examples of the disease include, for example, iscbemic disorders of cerebral nerve system such as vascular brain damages with one or more symptoms including sensory and motility disturbance, language disorder, memory disorder, dementia, convulsive attack, mental disorder and the like; ischemic heart diseases such as myocardial infarction; ischemic renal disturbances such as kidney failure; and ischemic hepatic disorders such as hepatic failure. These diseases also include those caused by pressure decrease, hypoxia or drug intoxication. Examples of the disease further include, for example, degenerative diseases caused by abnormality of mitochondria such as mitochondrial enzyme abnormality and mitochondrial gene mutation (Shigenaga et al., Proc. Natl. Acad. Sci., USA, 91, 10771–10778, 1994; Tanaka, M., et al., Naika (Medicine), 77, 881–887, 1996), and various taoxipathies.

Examples of the degenerative disease in which the involvement of mitochondrial functional abnormality has been verified or suggested include, for example, Parkinson's disease, Alzheimer's disease, amyotrophic lateral sclerosis (ALS), mitochondrial encephalomyopathy (Ohnishi, H. et al., Noshinkei (Cerebral Nerve), 44, 259–264, 1992), Niemann-Pick's disease. Examples of the toxic disease include, for instance, gas poisonings such as those by carbon monoxide gas, carbon dioxide gas, cyanide gas, alcoholic poisonings, drug poisonings, pesticide poisonings such as those by pyrethroid-type pesticide or organophosphorus pesticides, heavy metal poisonings, poisonings caused by toxins of natural animals or natural plants such as by puffer poison and mushroom poison.

It is known that calcium ions flow into cells in ischemic diseases or various toxic diseases (Zaidan, E. et al., J. Neurochem., 63, pp.1812–1819, 1994). It is also known that ATP synthesis in mitochondria depends on the electrochemical potential based on the difference in proton ($H^+$) concentrations inside and outside of mitochondria (Mitchell, P., Science, 206, 1148, 1979; Mitchell, P., FEBS Lett., 43, 184, 1974). Accordingly, the inventors of the present invention predicted that influx of calcium ions into the mitochondrial matrix may cause depolarization of mitochondrial membranes, and experimentally verified the hypothesis before the achievement of the present invention.

In addition, on the basis of the aforementioned fact, it is further predicted that mitochondrial membranes are depolarized by the influx of calcium ions into the mitochondrial matrix under the pathological conditions mentioned above, which may result in the reduction of the energy generation in mitochondria. Therefore, diseases resulting from a higher intracellular calcium ion concentration than the physiological concentration, in particular, diseases resulting from depolarization of mitochondrial membranes caused by the elevation of intracellular calcium ion concentration, are particularly suitable diseases applicable by the medicament of the present invention.

The first exemplary class of compounds that are suitable for the active ingredient of the medicament of the present invention includes 2-oxo-1-pyrrolidinylalkylcarboxylic acid amide compounds represented by the following formula.

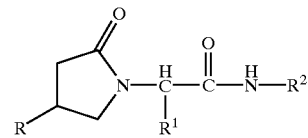

In the formula, R represents hydrogen atom or hydroxyl group, $R^1$ represents hydrogen atom or methyl group, and $R^2$ represents a pyridyl group or a phenyl group substituted with 1 to 3 substituents which may be the same or different. The substiituent on the phenyl group is selected from the group consisting of a halogen atom ("halogen atom" herein used may be any one of fluorine atom, chlorine atom, bromine atom, or iodine atom), trifluoromethyl group, nitro group, acetyl group, a straight- or branched-alkyl group having 1–4 carbon atoms, a straight- or branched alkoxyl group having 1–4 carbon atoms, a straight- or branched-alkylmercapto group having 1–7 carbon atoms, a substituted alkylmercapto group represented by the general formula: $-S-(CH_2)_n-$ CH(R³)(R⁴) wherein n represents 1 or 2, R³ represent hydrogen atom or methyl group, and R⁴ represents hydroxyl group, or an amino group represented by the general formula: —N(R⁸)(R⁹) wherein R⁸ represents hydrogen atom or methyl group, and R⁹ represents methyl group, benzyl group, or a substituted benzyl group, or R⁸ and R⁹ combine to each other to represent a substituted pyrrolidine ring together with the nitrogen atom in the formula, a sulphonyl group represented by the following general formula: —SO₂R⁵ wherein R⁵ represents amino group or an alkyl group having 1–3 carbon atoms, and an aminoethoxycarbonyl group represented by the formula: —COO(CH₂)₂—N(R⁶)(R⁷) wherein R⁶ and R⁷ independently represent hydrogen atom, methyl group, or ethyl group.

Specific examples of the substituent of the phenyl group include, for example, a halogen atom such as chlorine atom and fluorine atom; an alkyl group such as methyl group, ethyl group, n-propyl group, sec-butyl group, and n-butyl group; an alkoxyl group such as methoxy group and isopropoxy group; an alkylmercapto group such as methylmercapto group, n-propylmercapto group, isopropylmercapto group, sec-butylmercapto group, and n-heptylmercapto group; a substituted alkylmercapto group such as 2-hydroxypropylmercapto group, 2-(N,N-dimethylamino)-propylmercapto group, and 2-(N-methyl-N-benzylamino)-ethylmercapto group; an N-methyl-N-benzylaminoalkylmercapto group represented by the general formula: —S—(CH₂)ₙ—CH(R³)—N(R⁸)(R⁹) wherein the substituted benzyl group represented by R⁹ is benzyl group substituted with methoxy group, such as 2-N-methyl-N-(3, 4-dimethoxybenzyl)-amino)-ethylmercapto group; a 1-pyrrolidinylalkylmercapto group represented by the general formula: —S—(CH₂)ₙ—CH(R³)—N(R⁸)(R⁹) wherein the substituted pyrrolidine ring represented by R⁸ and R⁹ is the ring substituted with 2-oxo group, such as 2-(2-oxo-1-pyrrolidinyl)-ethylmercapto group; 2-(N,N-diethylamino)-ethoxycarbonyl group and the like. Unsubstituted pyridyl group may preferably be used as the pyridyl group represented by R², and any one of 2-pyridyl group, 3-pyridyl group or 4-pyridyl group may be used.

The second exemplary class of compounds suitable as the active ingredient of the medicament of the present invention includes a compound selected from the group consisting of:
(1) 2-oxo-1-pyrrolidinylacetic acid 2,6-dimethylanilide;
(2) 4-hydroxy-2-oxo-1-pyrrolidinylacetic acid 2,6-diethylanilide;
(3) 4-hydroxy-2-oxo-1-pyrrolidinylacetic acid 2,6-dimethylanilide;
(4) 2-[2-oxo-pyrrolidinyl]propionic acid N-3-pyridinylamide;
(5) 2-oxo-1-pyrrolidinylacetic acid 4-isopropylmercaptoanilide;
(6) 2-[2-oxo-1-pyrrolidinyl]-1-propionic acid 4-(2-butylmercapto)-anilide;
(7) 2-[2-oxo-1-pyrrolidinyl]propionic acid 4-isopropylanilide;
(8) 2-[2-oxo-1-pyrrolidinyl]propionic acid 2,4-dimethylanilide;
(9) 2-[2-oxo-1-pyrrolidinyl]propionic acid 2,4,6-trimethylanilide;
(10) 2-[2-oxo-1-pyrrolidinyl]propionic acid 2-methoxy-5-methylanilide;
(11) 2-[2-oxo-1-pyrrolidinyl]propionic acid 2,6-dichloroanilide;
(12) 2-pyrrolidoneacetamide;
(13) 1-anisoyl-2-pyrrolidinone;
(14) 4-hydroxy-2-oxo-1-pyrrolidineacetamide and other.

The compounds disclosed in the Japanese Patent Publication No. Hei 3-46466/1992, Table 3 on pages 10–19, are also typical compounds falling within the second class of compounds as well as the aforementioned specific compounds.

Particularly preferred compounds falling within the second class of compounds include; 2-oxo-1-pyrrolidinylacetic acid 2,6-dimethylanilide {N-(2,6-dimethylphenyl)-2-(2-oxo-1-pyrrolidinyl)acetamide, generic name: Nefiracetam}; 2-pyrrolidoneacetamide; 1-anisoyl-2-pyrrolidinone; and 4-hydroxy-2-oxo-1-pyrrolidineacetamide.

The third exemplary class of compounds suitable as the active ingredient of the medicament of the present invention includes compounds represented by the following formula.

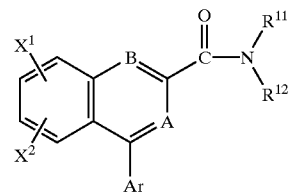

In the formula, R¹¹ and R¹² independently represents a straight- or branched-alkyl group having 1–6 carbon atoms, a cycloalkyl group having 3–7 carbon atoms, a phenylalkyl group whose alkyl moiety has 1–3 carbon atoms, or a cycloalkyl-substituted alkyl group, or represents an alkenyl group or an alkynyl group having 3–6 carbon atoms in which a double bond or a triple bond is not present at the 1–2 position relative to the nitrogen atom; A and B independently represent N or CH; X¹ and X² independently represent a halogen atom, a straight- or branched-alkyl group having 1–3 carbon atoms, a straight- or branched-alkoxyl group having 1–3 carbon atoms, nitro group, or trifluoromethyl group; Ar represents phenyl group, a pyridyl group, a thienyl group, or a substituted phenyl group (the substituent on the phenyl group consists of 1 or 2 functional groups selected from the group consisting of a halogen atom, a straight- or branched-alkyl group having 1–4 carbon atoms, a straight- or branched-alkoxyl group having 1–4 carbon atoms, a straight- or branched-alkylthio group having 1–4 carbon atoms, trifluoromethyl group, and nitro group).

Among the compounds of this class of compounds, preferred compounds include those wherein X¹ and X² are hydrogen atoms, Ar is a substituted phenyl group, B is CH, A is N, and R¹¹ and R¹² are independently a straight- or branched-alkyl group having 1–6 carbon atoms. More preferred compounds include those wherein X¹ and X² are hydrogen atoms, Ar is a chlorophenyl group, B is CH, A is N, R¹¹ is methyl group, and R¹² is a straight- or branched-alkyl group having 1–6 carbon atoms. Particularly preferred compounds are N-methyl-N-(1-methylpropyl)-(2-chlorophenyl)isoquinoline-3-carboxamide, and optically active substances thereof, N-methyl-N-(1-(S)-methylpropyl)-(2-chlorophenyl)isoquinoline-3-carboxamide and N-methyl-N-(1-(R)-methylpropyl)-(2-chlorophenyl)isoquinoline-3-carboxamide. These compounds are disclosed in Examples 44 and 45 of the Japanese Patent Unexamined Publication (KOKAI) 58-201756/1983.

The fourth exemplary class of compounds suitable as the active ingredient of the medicament of the present invention includes compounds represented by the following formula.

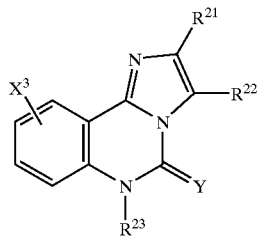

In the formula, $R^{21}$ represents unsubstituted phenyl group, a substituted phenyl group (the substituent on the phenyl group consists of 1 or 2 substituents selected from the group consisting of a halogen atom, a straight- or branched-alkyl group having 1–6 carbon atoms, and a straight- or branched-alkoxy group having 1–6 carbon atoms), or a thienyl group; $R^{22}$ represents hydrogen atom, a halogen atom, a straight- or branched-alkyl group having 1–6 carbon atoms, or a substituted straight- or branched-alkyl group having 1–6 carbon atoms (the substituent is selected from the group consisting of amino group, an alkylamino group, and a dialkylamino group); $R^{23}$ represents a group represented by the formula: $(R^{24})(R^{25})N$—CO—Q— wherein Q represents a straight- or branched-alkylene group having 1–6 carbon atoms, and $R^{24}$ and $R^{25}$ independently represent a straight- or branched-alkyl group having 1–6 carbon atoms, unsubstituted phenyl group, or a substituted phenyl group (the substituent on the phenyl group consists of 1 or 2 substituents selected from the group consisting of a halogen atom, a straight- or branched-alkyl group having 1–6 carbon atoms, and a straight- or branched-alkoxyl group having 1–6 carbon atoms); $X^3$ represents hydrogen atom or a halogen atom; and Y represents oxygen atom or sulfur atom.

Among the compounds falling within this class of compounds, preferred compounds include those wherein $R^{21}$ is a substituted phenyl group (the substituent on the phenyl group consists of 1 or 2 substituents selected from the group consisting of a halogen atom, a straight- or branched-alkyl group having 1–6 carbon atoms, and a straight- or branched-alkoxyl group having 1–6 carbon atoms); $R^{22}$ is a halogen atom; $R^{23}$ is a group represented by the formula: $(R^{24})(R^{25})N$—CO—Q— wherein Q represents a straight- or branched-alkylene group having 1–6 carbon atoms, and $R^{24}$ is a straight- or branched-alkyl group having 1–6 carbon atoms, $R^{25}$ represents unsubstituted phenyl group or a substituted phenyl group (the substituent on the phenyl group consists of 1 or 2 substituents selected from the group consisting of a halogen atom, a straight- or branched-alkyl group having 1–6 carbon atoms, and a straight- or branched-alkoxyl group having 1–6 carbon atoms); $X^3$ is hydrogen atom; and Y is oxygen atom. More preferred compounds include those wherein $R^{21}$ is a chlorophenyl group; $R^{22}$ is bromine atom; $R^{23}$ is a group represented by the formula: $(R^{24})(R^{25})N$—CO—Q— wherein Q is a straight- or branched-alkylene group having 1–6 carbon atoms, $R^{24}$ is a straight- or branched-alkyl group having 1–6 carbon atoms, and $R^{25}$ is an unsubstituted phenyl group; $X^3$ is hydrogen atom; and Y is oxygen atom.

A particularly preferred compound is 2-(3-chlorophenyl)-3-bromo-6-(N-methyl-N-phenylacetamido)-5-oxo-5,6-dihyroimidazo[1,2-c]quinazoline. This compound is disclosed as compound No. 42 in Examples of the Japanese Patent Unexamined Publication (KOKAI) No. Hei 4-217682/1992.

The compounds falling within the aforementioned exemplary classes of compounds can readily be prepared according to the methods described in the Japanese Patent Unexamined Publication (KOKAI) Nos. Sho 56-2960/1981, Sho 61-280470/1986, Hei 4-160496/1992, Sho 58-201756/1983, Hei 4-217682/1992 and other. As for the aforementioned pyrrolidinylacetamide derivatives disclosed in the Japanese Patent Publication (KOKOKU) No. Hei 3-46466/1991, their biological activities are known, for example, improving activity on cerebral function (Japanese Patent Publication (KOKOKU) No. Sho 62-5404/1987), improving effect on dementia resulting from Alzheimer's disease (Japanese Patent Unexamined Publication (KOKAI) No. Hei 5-163144/1993), improving effect on cerebrovascular dementia (Japanese Patent Unexamined Publication (KOKAI) No. Hei 5-163145/1993), anticonvulsant activity observed in E1 mouse (Nakamoto et al, The 17th Japan Neurology Convention, Dec. 7–9, 1993, Program Abstracts p.84, Subject number P1A20). In addition, these compounds are also known to have affinity for the mitochondria benzodiazepine receptor (MBR) present in mitochondrial membranes (Neurosci. Res. Suppl. 17, S88, 1992, 2–71). However, any effect of the compounds on the mitochondrial membrane potential has not been known so far.

As the active ingredient of the medicament of the present invention, a compound either in the form of a free compound or a physiologically acceptable salt form may be used. Any hydrate or any solvate thereof may also be used. Examples of the physiologically acceptable salt include, for instance, acid addition salts including mineral acid salts such as hydrochloride, hydrobromide, hydriodide, sulfate, nitrate, and phosphate, and organic acid salts such as acetate, maleate, fumarate, citrate, oxalate, succinate, tartrate, malate, mandelate, methanesulfonate, p-toluenesulfonate, and 10-camphorsulfonate. When a compound used as the active ingredient of the medicament of the present invention has one or more asymmetric carbon atoms, the stereochemistry of the asymmetric carbon atom is not particularly limited. Any optically active substances, any mixtures of optical isomers or racemates may be used. Any mixture of diastereoisomers based on two or more asymmetric carbon atoms may also be used.

The route of administration of the medicament of the present invention is not particularly limited, and the medicament may be administered orally or parenterally. A compound as an active ingredient, e.g., a compound of the aforementioned formula (I), per se, may be administered as the medicament of the present invention. However, the medicament may preferably be provided as a pharmaceutical composition comprising a compound as an active ingredient together with one or more pharmacologically and pharmaceutically acceptable additives for pharmaceutical preparations. Examples of the pharmacologically and pharmaceutically acceptable additives include, for example, excipients, disintegrators or disintegrating aids, binders, lubricants, coating agents, colorants, diluents, base materials, dissolving agents or dissolving aids, isotonicities, pH modifiers, stabilizers, propellants, adhesives and other. Examples of the pharmaceutical compositions suitable for oral administrations include, for example, tablets, capsules, powders, subtilized granules, granules, liquids, syrups and other. Examples of the pharmaceutical compositions suitable for parenteral administrations include, for example, injections, drip infusions, suppositories, inhalants, patehes and other. The medicament, of the present invention may contain one or more active ingredients.

The doses of the medicament of the present invention are not particularly limited, and suitable doses can be chosen depending on various factors including therapeutic or preventive or prophylactic purpose, nature of a disease, the age and condition of a patient, the route of administration or other. In general, for oral administrations, the dose may be about 10 mg to 1,000 mg, preferably about 60 mg to 900 mg per day for an adult. The acute toxicity of 2-oxo-1-pyrrolidinylacetic acid 2,6-dimethylanilide (non-proprietary name; Nefiracetam), which is most preferably used according to the present invention, is 2,005 mg/kg (male mouse, p.o.), and the compound has been verified to have high safety (Japanese Patent Unexamined Publication (KOKAI) No. Hei 5-163144/1993).

EXAMPLES

The present invention will be explained more specifically by referring to the following examples. However, the scope of the present invention is not limited to these examples. The test procedure in the examples was according to the method of Hare et al. (Hare, M. F., et. al., JPET, 266, pp.1626–1635, 1993) unless otherwise indicated. In the examples, "Nefiracetam" means 2-oxo-1-pyrrolidinylacetic acid 2,6-dimethylanilide, and "Ro5-4864" means the mitochondrias benzodiazepine receptor agonist, (7-chloro-5-(4-chlorophenyl)-1,3-dihydro-1-methyl-2H-1,4-benzodiazepin-2-one: TIPS, December, pp. 506–511, 1986).

Example 1

Determination of the Intracellular $Ca^{2+}$ Concentration

Changes in the intracellular $Ca^{2+}$ concentration caused by Ro5-4864 was studied. Cultured cells (NG108-15 cells: nerve cell x neuroglia cell hybrid) were cultured in DMEM culture medium, and further cultured in Flexiperm Disc (Heraeus Biotechnology) provided with a cover glass and used in the following described below. The cultured NG 108-15 cells were added with Ro5-4864 at final concentration of 50 mM. A fluorescent remedicament, fura2-AM (1-(6-amino-2-(5-carboxy-2-oxazoly-5-benzofuranyloxy)-2-(2-amino-5-methylphenoxy)-ethane-N,N,N',N'-teraacetic acid, pentaacetoxymethyl ester, Dojindo Laboratories) was dissolved in DMSO (Dimethylsulfoxide, Nakarai Chemical) to prepare a 1 mM solution, and this solution was diluted 200 times with HBS (Herpes-saline solution, composition: NaCl; 130 mM; KCl: 5.4 mM; $CaCl_2$: 1.8 mM; $MgSO_4$: 0.8 mM; D-glucose: 20 mM; $Na^+$-HEPES; 20 mM, pH 7.3) to prepare a fluorescent reagent solution (final concentration of fra2-AM: 5 $\mu$M).

For the determination of intracellular $Ca^{2+}$ concentrations, the culture medium was removed from the Petri dish where the NG108-15 cells were cultured, and the dish was washed twice with HBS. The cultured cells were added with the 5 $\mu$M fura2-AM solution prepared above, put in a carbon dioxide gas incubator for 30 minutes, and then washed with HBS five times to remove the added fura2-AM solution. Finally, 1 ml of HBS was added to the Flexiperm, and the intracellular $Ca^{2+}$ concentration was measured by ARGUS-50/CA (Hamamatsu Photonics). According to this measurement, the fluorescence of $Ca^{2+}$-bound type fura-2 emitted at an excitation wavelength of 340 nm and the fluorescence of $Ca^{2+}$-free type fura-2 emitted at an excitation wavelength of 380 nm were measured as a pair at a constant interval for the fura-2 loaded cultured cells, and their relative ratio (ratio of fluorescence intensity) was used to analyze the intracellular $Ca^{2+}$ dynamics (concentration). An increase in the 340 nm excited fluorescence due to the binding of intracellular calcium ions to the fura2-AM, and a decrease in the 380 nm excited fluorescence were recorded by imaging and the ratio of fluorescence intensity between the fluorescence images was obtained. The effect of Ro5-4864 on the intracellular $Ca^{2+}$ concentration is shown in FIG. 1. From these results, it is clearly understood that the intracellular $Ca^{2+}$ concentration sharply increases by the addition of Ro5-4864.

Example 2

Determination of the Mitochondrial Membrane Potential

Figure 2:
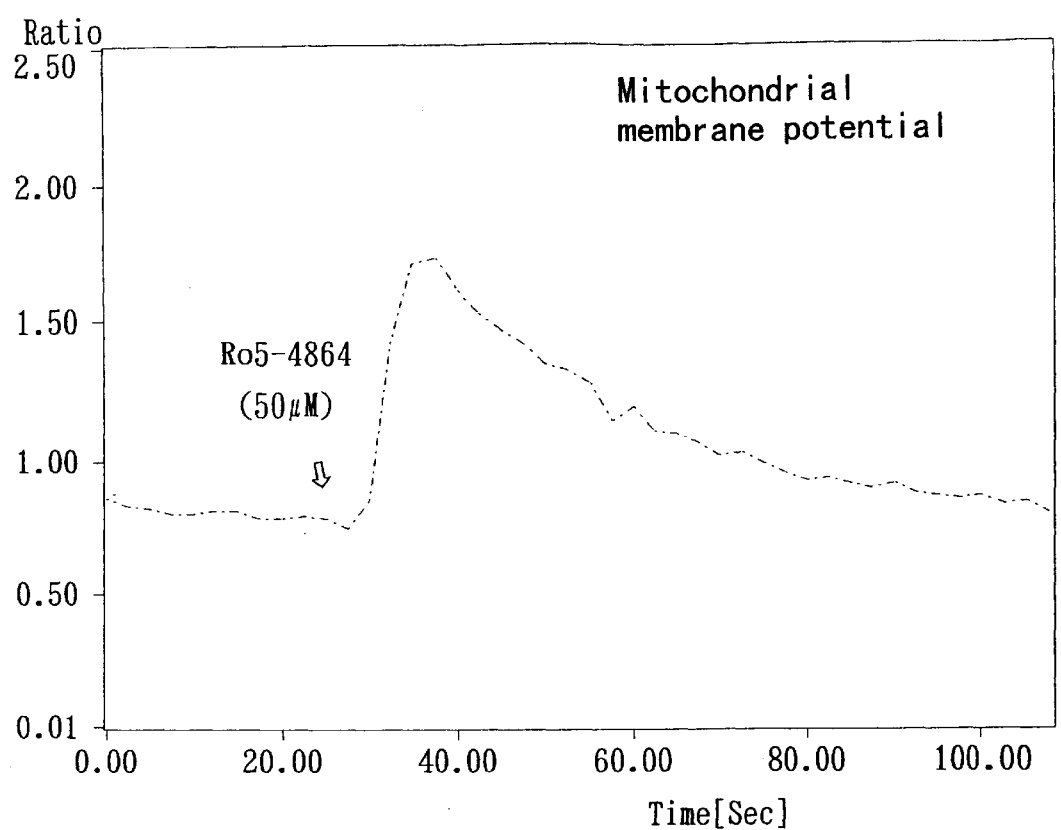
FIG. 2 shows an effect of Ro5-4864 on mitochondrial membrane potential.

Rhodamine 123 (2-[6-amino-3-imino-3H-xanthen-9-yl]-benzoic acid methyl ester, Sigma) was dissolved and diluted with HBS to prepare a solution at a final concentration of 10 $\mu$M. The culture medium was removed from NG108-15 cells cultured in a Petri dish, and the dish was washed twice with HBS. The Rhodamine 123 solution was stirred again, and added to the cultured cells, and the cells were put in a carbon dioxide gas incubator for ten minutes. Then, the cells were washed five times with HBS to remove the added Rhodamine 123 solution. Subsequently, the Flexiperm Disc containing the cells was added with HBS (1 ml), and again put in a carbon dioxide incubator for ten minutes. Finally, the cells were washed with HBS once, and used for the experiment. ARGUS-50/CA (Hamamatsu Photonics) was used for the determination of intracellular $Ca^{2+}$ concentration. In the experiment for determination of the mitochondrial membrane potential, Ro5-4864 (50 $\mu$M) was added to the NG108-15 cells, and changes in the potential were measured by ARCUS-50/CA with given intervals. From the result shown in FIG. 2, it was found that the mitochondrial membrane potential was remarkably decreased by the addition of Ro5-4864 and the membranes were depolarized. In the figure, the longitudinal axis represents the ratio of fluorescence intensity in the same manner as FIG. 1. For this experiment, the fluorescence intensity was recorded from the initially obtained image and used as a standard (ratio= 1.0) to indicate relative ratios of fluorescence intensities in images recorded later along the longitudinal axis.

The endoplasmic reticulum is known as a cell organelle participating in intracellular $Ca^{2+}$ control, and two mechanisms are known as $Ca^{2+}$-releasing mechanism from the endoplasmic reticulum, i.e., $Ca^{2+}$ release by inositol tris-phosphate (a stimulant: bradykinin (BK)), and $Ca^{2+}$-induced $Ca^{2+}$ release (a stimulant: caffeine (Caff)). In order to study the relationship between the increase in the intracellular $Ca^{2+}$ concentration observed in Example 1, which were caused by the addition of Ro5-4864, and the decrease in the mitochondrial membrane potential observed in Example 2, similar experiments were performed after intracellular $Ca^{2+}$ derived from endoplasmic reticulum was depleted by treatments with bradykinin and caffeine to examine whether or not the $Ca^{2+}$ observed in Example 1 was $Ca^{2+}$ accumulated in the mitochondrial matrix. By a method similar to that of Example 1, the intracellular $Ca^{2+}$ concentration was measured.

Example 3

Effect of Ro5-4864 on Cells Treated with Bradykinin and Caffeine

Figure 3:
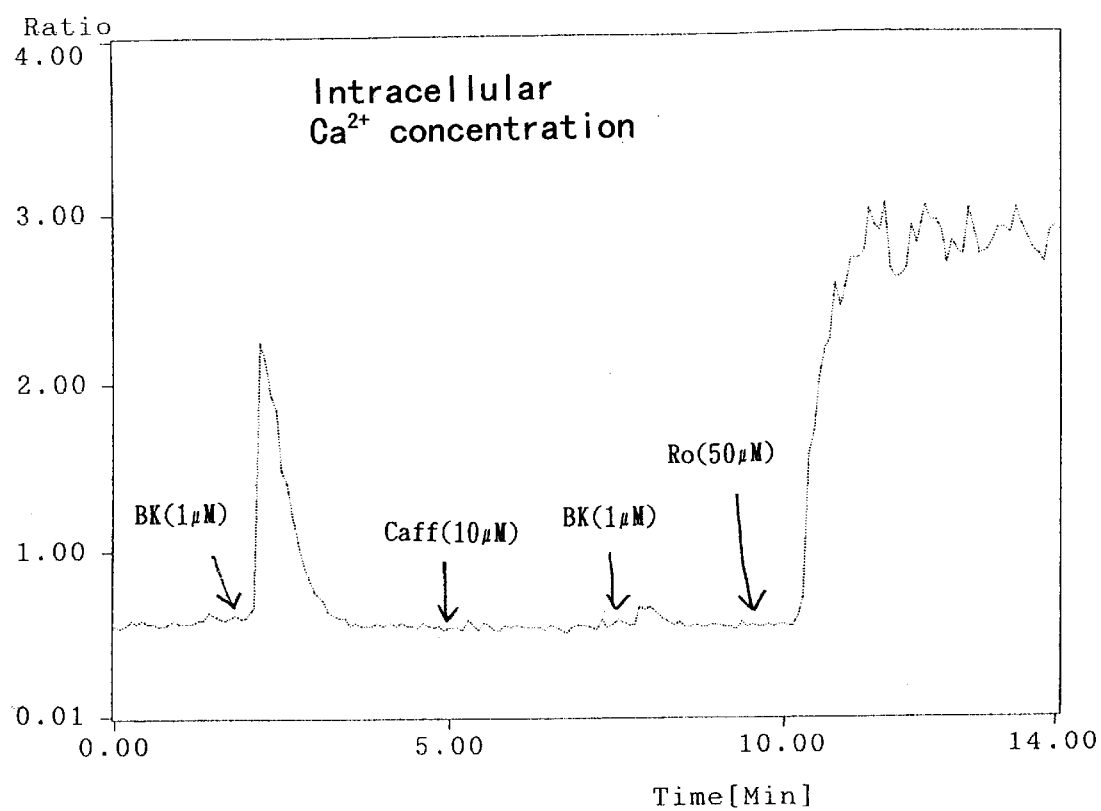
FIG. 3 shows an effect of Ro5-4864 on intracellular $Ca^{2+}$ concentration in NG108-15 nerve cells treated with bradykinin and caffeine.

FIG. 3 shows the effect of Ro5-4864 on the intracellular $Ca^{2+}$ concentration in the NG108-15 cells treated with bradykinin and caffeine. First, when bradykinin (BK, 1 $\mu$M) was applied, which is known to induce the release of $Ca^{2+}$ from the endoplasmic reticulum to cytoplasm through a receptor, remarkable increase of intracellular $Ca^{2+}$ concentration was observed. Then, after caffeine (Caff, 10 μM) was applied, BK was applied again successively, and as a result, the intracellular $Ca^{2+}$ concentration was not increased. These results can be interpreted that the intracellular $Ca^{2+}$ derived from the endoplasmic reticulum was depleted by the first BK application. When Ro5-4864 (50 μM) was applied under this condition, the intracellular $Ca^{2+}$ concentration was markedly elevated. Bradykinin is not considered to act on the mitochondrion, i.e., the other storage site of the intracellular $Ca^{2+}$. Accordingly, it was demonstrated that the elevation of the intracellular $Ca^{2+}$ concentration caused by Ro5-4864 was derived from mitochondria.

Figure 4:
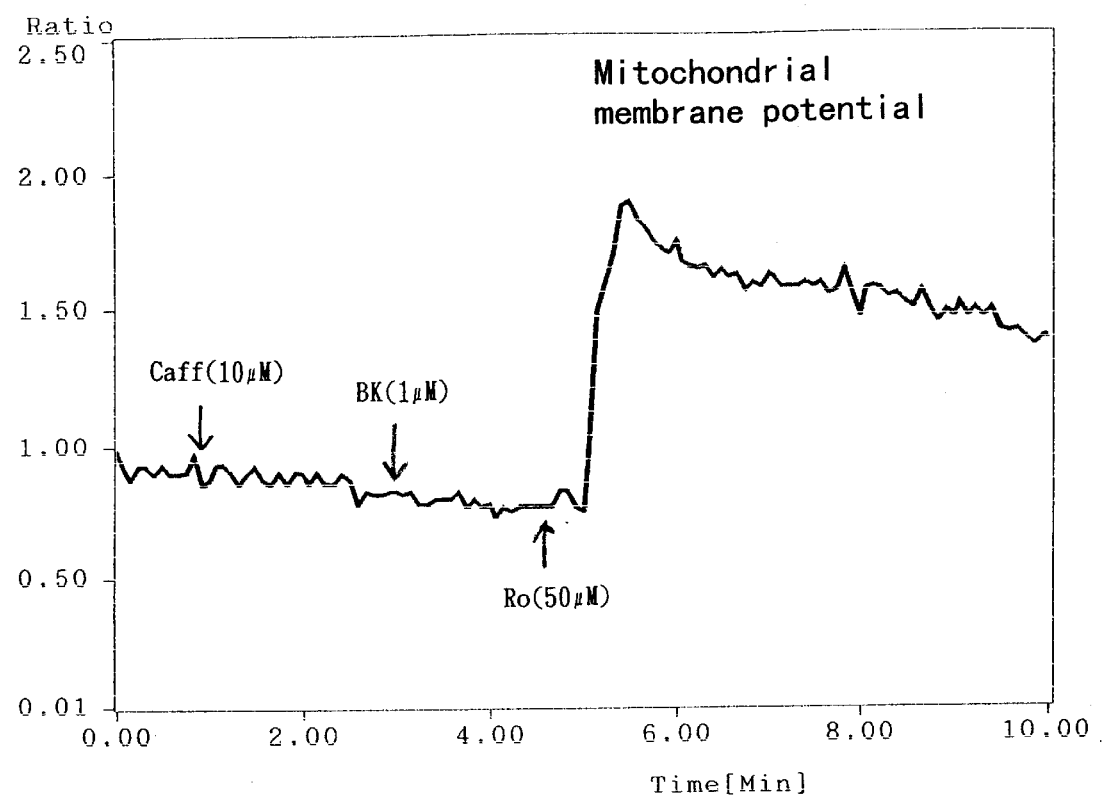
FIG. 4 shows an effect of Ro5-4864 on mitochondrial membrane potential in NG108-15 nerve cells treated with bradykinin and caffeine.

The mitochondrial membrane potential was measured in the same manner as Example 2. When caffeine (10 μM) and bradykinin (1 μM) were applied, no alteration was recognized in the mitochondrial membrane potential. However, a remarkable decrease in the mitochondrial membrane potential was recognized when Ro5-4864 (50 μM) was applied. These results verified the depolarization of mitochondrial membranes (FIG. 4).

Example 4

Figure 5:
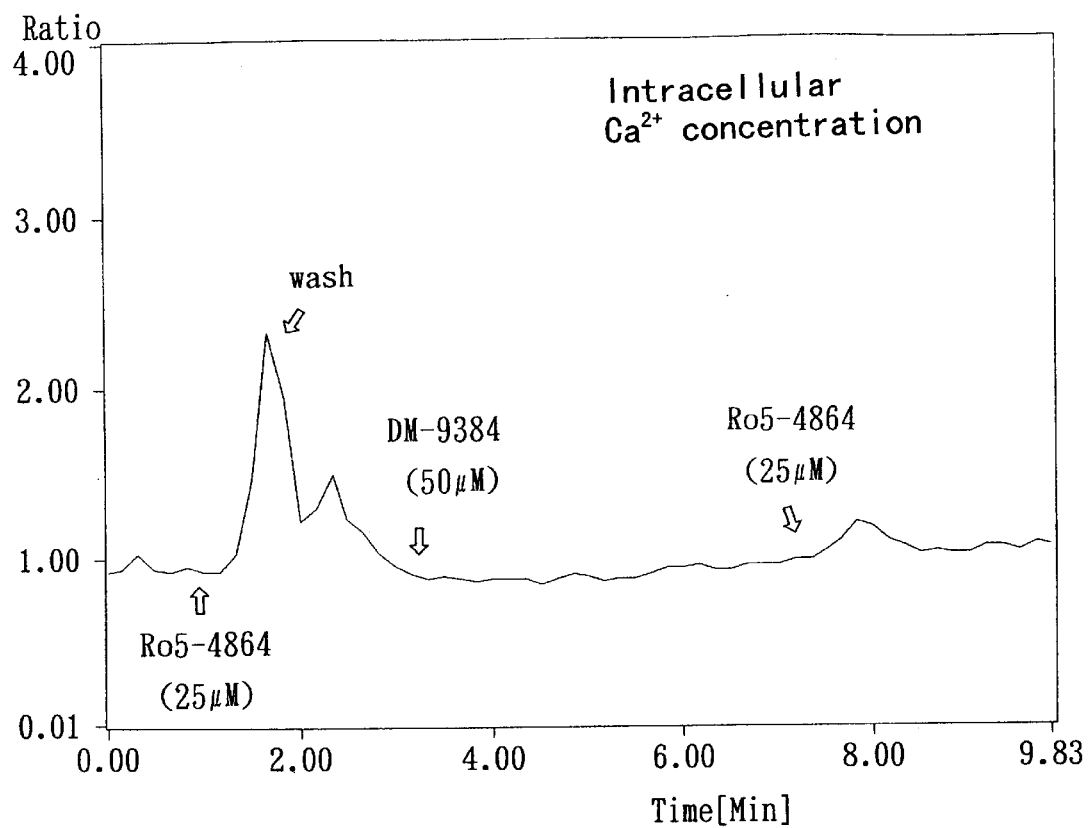
FIG. 5 shows inhilition by a medicament, of the present invention caused by Ro5-4864.

Effect of Ro5-4864 on the Intracellular $Ca^{2+}$ Concentration in Nefiracetam Treated Cells When Ro5-4864 (25 μM) was applied, an elevation of the intracellular $Ca^{2+}$ concentration was observed (FIG. 5, first peak). After the observation of the response of the above reaction, the cells were washed, and then applied with Nefiracetam (50 μM) as the medicament of the present invention. As a result, no change of intracellular $Ca^{2+}$ concentration was observed. When Ro5-4864 (25 μM) was added in the presence of Nefiracetam, almost no change in the intracellular $Ca^{2+}$ concentration was observed (FIG. 5). These results indicate that the medicament of the present invention inhibited elevation of intracellular $Ca^{2+}$ concentrations caused by Ro5-4864 (25 μM).

Example 5

Figure 6:
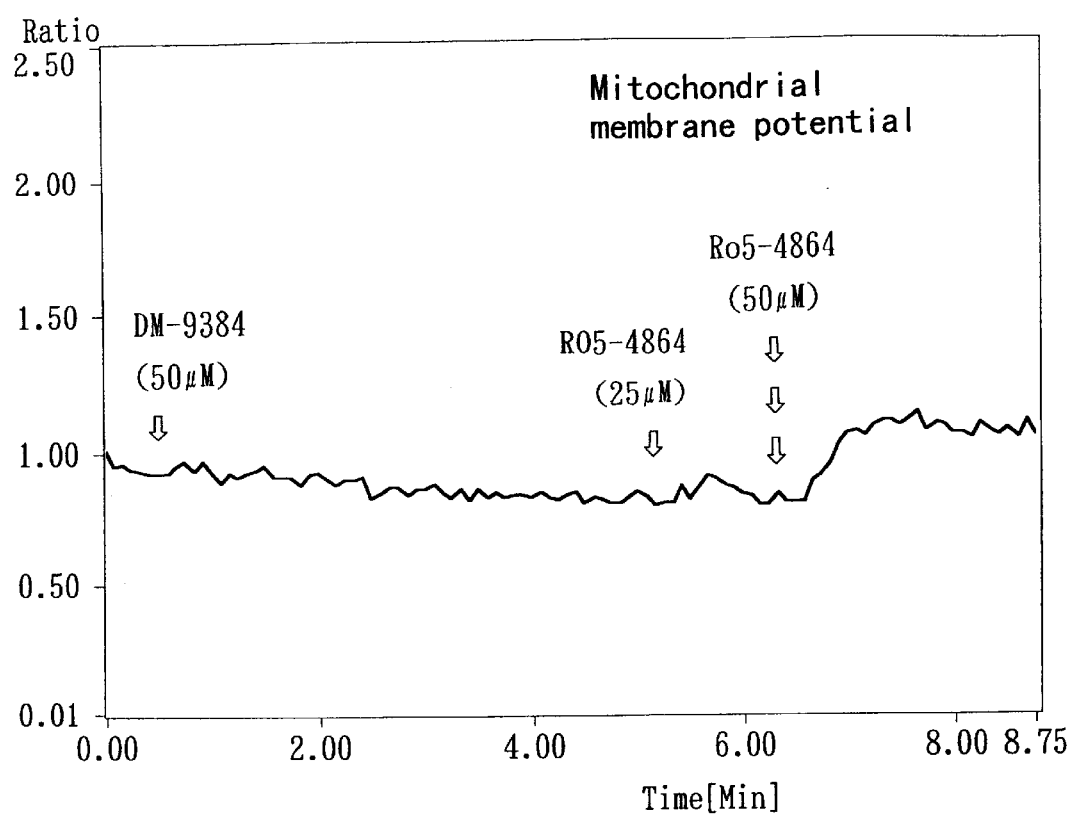
FIG. 6 shows inhibition by a medicament of the present invention (Nefiracetam) against the depolarizing effect of Ro5-4864 on mitochondrial membranes.

Effect of Ro5-4864 on the Mitochondrial Membrane Potential in Nefiracetam Treated Cells Effect of the medicament of the present invention on the mitochondrial membrane potential was examined in the same manner as that of Example 2. When Nefiracetam (50 μM) was applied first, no change was observed in the mitochondrial membrane potential. When Ro5-4864 (25 μM) was applied in the presence of Nefiracetam, almost no change in the mitochondrial membrane potential was observed (FIG. 6). These results indicate that the medicament of the present invention inhibited the depolarizing effect of Ro5-4864 (25 μM) on mitochondrial membranes. When Ro5-4864 was applied at a higher concentration (50 μM) in a similar experiment, the depolarizing effect on mitochondirial membranes was recognized, although the effect was weak (FIG. 6).

Example 6

Effect of Ro5-4864 on the Intracellular $Ca^{2+}$ Concentration in PK 11195 Treated Cells N-Methyl-N-(1-methylpropyl)-(2-chlorophenyl) isoquinoline-3-carboxamide (PK 11195, racemate) was prepared in a similar manner to the method described in the Japanese Patent Unexamined Publication [KOKAI] No. Sho 58-201756/1983, Example 45. m.p. 133–134° C. (CHCl$_3$-EtOH), Anal. Calcd. for $C_{21}H_{21}ClN_2O_2$: C, 71.48%; H, 6.00%; N, 7.94% Found C, 71.19%; H, 5.94%; N, 8.06%.

Figure 7:
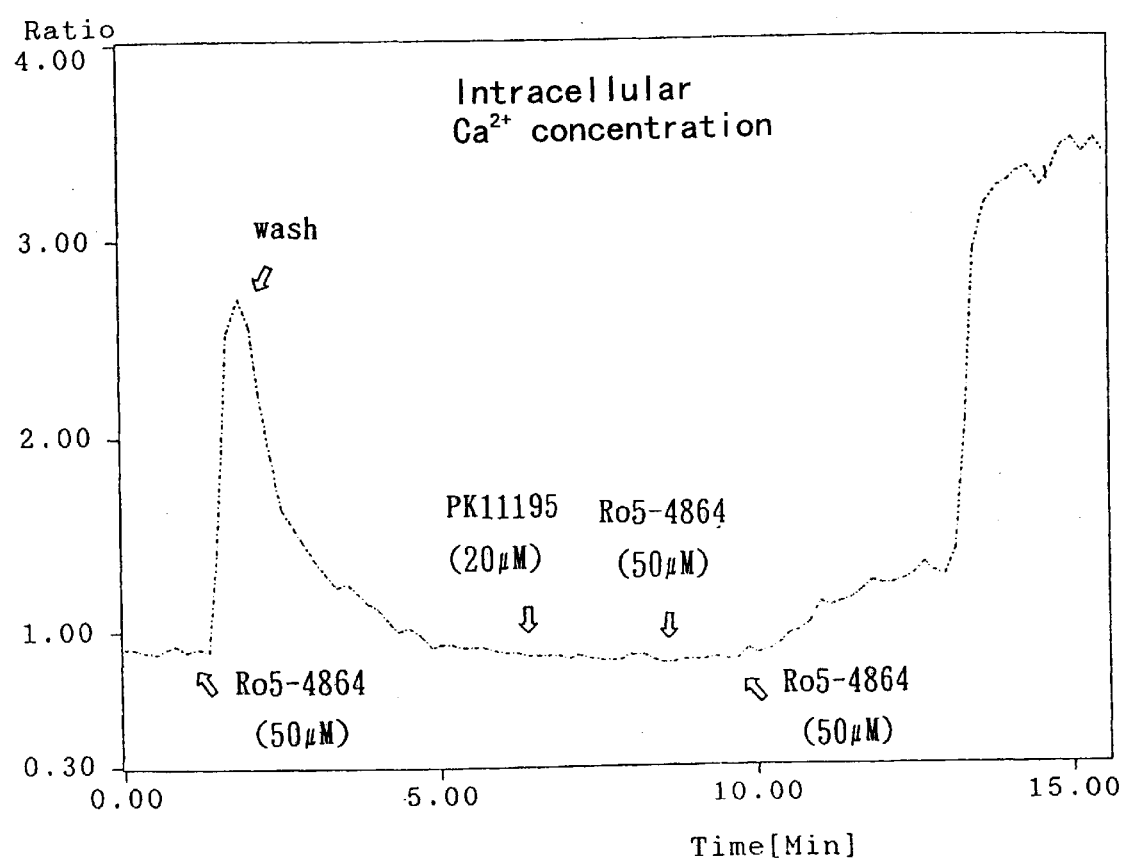
FIG. 7 shows inhibition by a medicament of the present invention (PK 11195) against the depolarizing effect of Ro5-4864 on mitochondrial membranes, and the result of correlation between mitochondrial membrane depolarization and intracellular $Ca^{2+}$ concentration by activation of the mitochondrial benzodiazepine receptor (MBR).

When Ro5-4864 (50 μM) was applied, an elevation of the intracellular $Ca^{2+}$ concentration was observed (FIG. 7, first peak), and then, the cells were applied with Ro5-4864 after pretreatment with PK11195 (20 μM). As a result, the enhancing effect on intracellular $Ca^{2+}$ concentrations was not observed. The result indicates that the depolarizing effect on mitochondrial membranes and the intracellular $Ca^{2+}$ concentration are correlated through the activation of MBR (mitochondrial benzodiazepine receptor) by PK 11195.

Example 7

Figure 8:
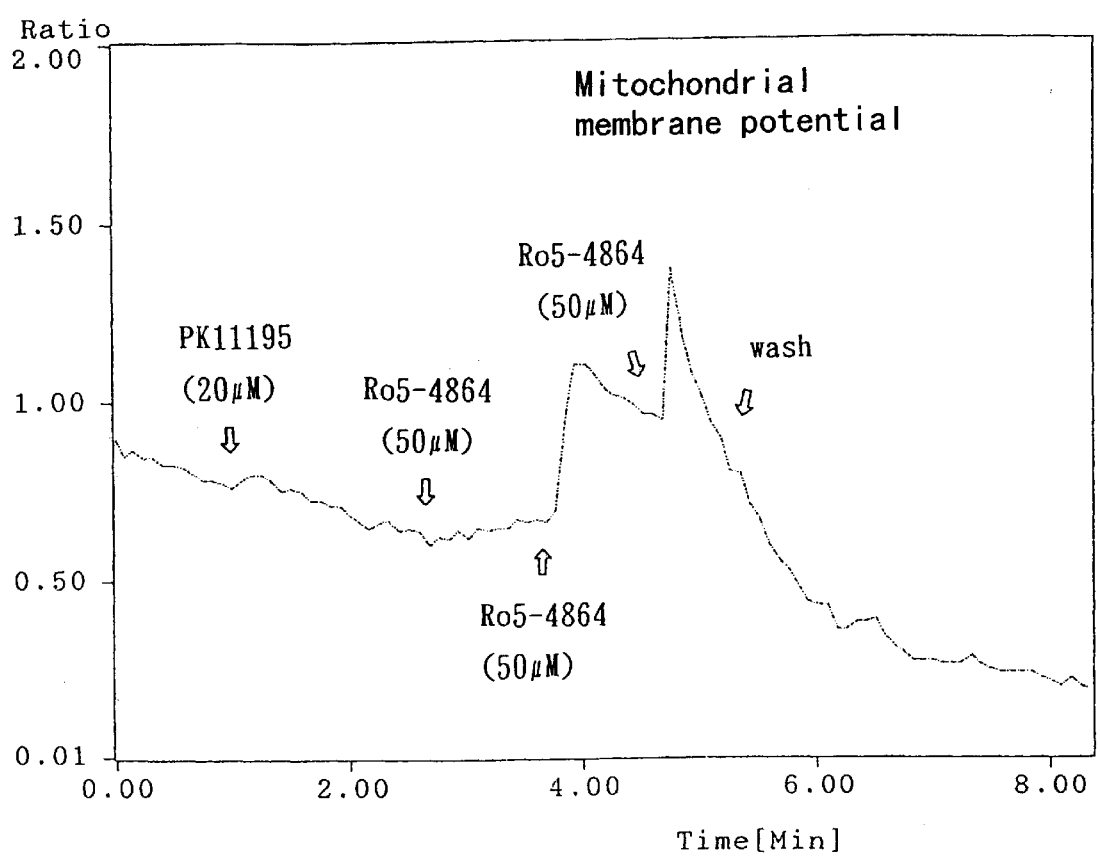
FIG. 8 shows inhibition by a medicament of the present invention (PK 11195) against the effect of Ro5-4864 on mitochondrial membrane potential, and the results of competitive actions on MBR by the medicament of the present invention and Ro5-4864.

Effect of Ro5-4864 on the Mitochondrial Membrane Potential in PK 11195 Treated Cells Effect of the medicament, of the present invention on the mitochondrial membrane potential was examined in the same manner as that of Example 2. When PK 11195 (20 μM) was applied first, no change was observed in the mitochondrial membrane potential. When Ro5-4864 (50 μM) was applied in the presence of PK 11195 (20 μM), almost no change in the mitochondrial membrane potential was observed. However, repeated addition of Ro5-4864 afterwards induced the depolarization and shifted the mitochondrial membrane potential upward. These results suggest a possibility that the medicament of the present invention and Ro5-4864 competitively act on MBR (FIG. 8).

Example 8

Effect of Ro5-4864 on the Intracellular $Ca^{2+}$ Concentration in NCS-1044-90 Treated Cells 2-(3-Chlorophenyl)-3-bromo-6-(N-methyl-N-phenylacetamido)-5-oxo-5,6-dihydroimidazo[1,2-c]quinazoline (NCS-1044-90) was prepared in a similar manner to the method described in Japanese Patent Unexamined Publication [KOKAI] No. Hei 4-217682/1992, Example 42. m.p. 225–227° C. (Et$_2$O) Anal. Calcd. for $C_{25}H_{18}BrClN_4O_2$ C, 57.55%; H, 3.48%; N, 10.74% Found C, 57.93%; H, 3.53%; N, 10.91%.

Figure 9:
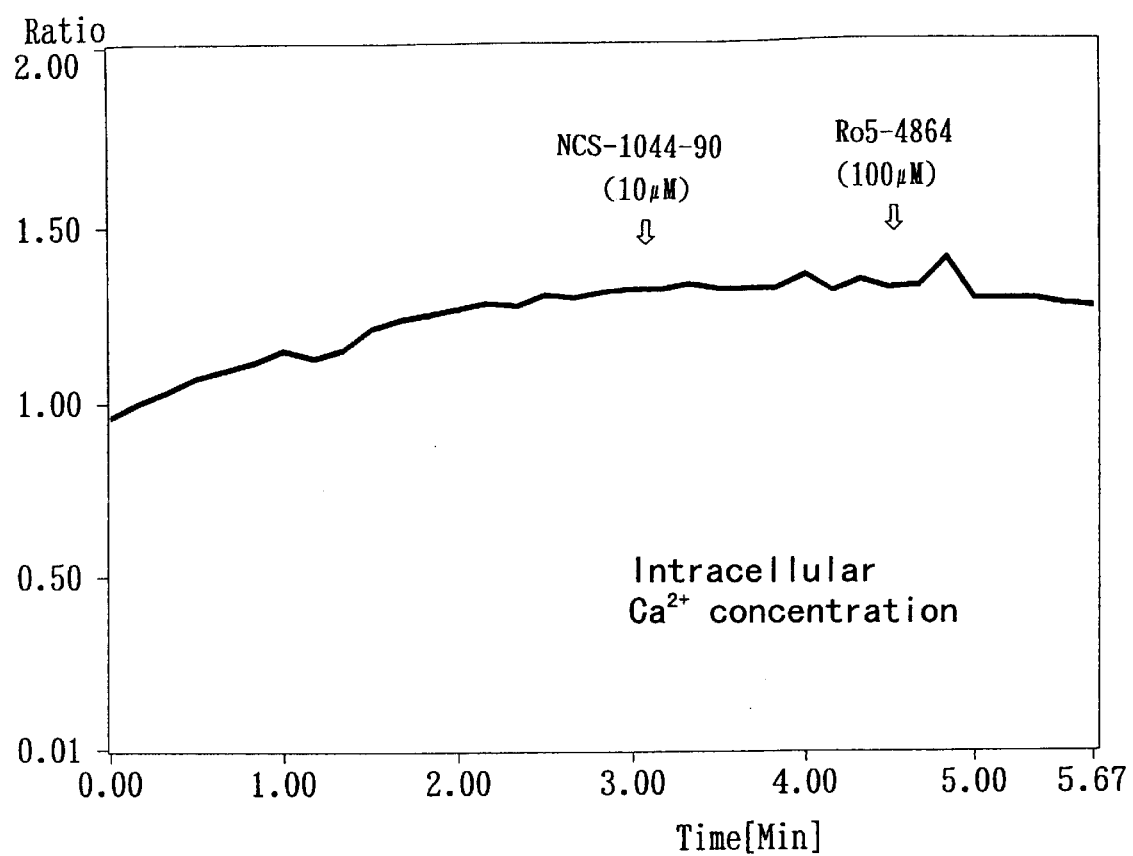
FIG. 9 shows an effect of Ro5-4864 on intracellular $Ca^{2+}$ concentration in cells treated with a medicament of the present invention (NCS-1044-90).

Ro5-4864 (100 μM) was applied to the cells that had been applied with NCS-1044-90 (10 μM) beforehand, and changes in the intracellular Ca2+ concentration were examined. As a result, only a very small elevation of the intracellular $Ca^{2+}$ concentration was observed even after the addition of Ro5-4864 (FIG. 9).

Example 9

Figure 10:
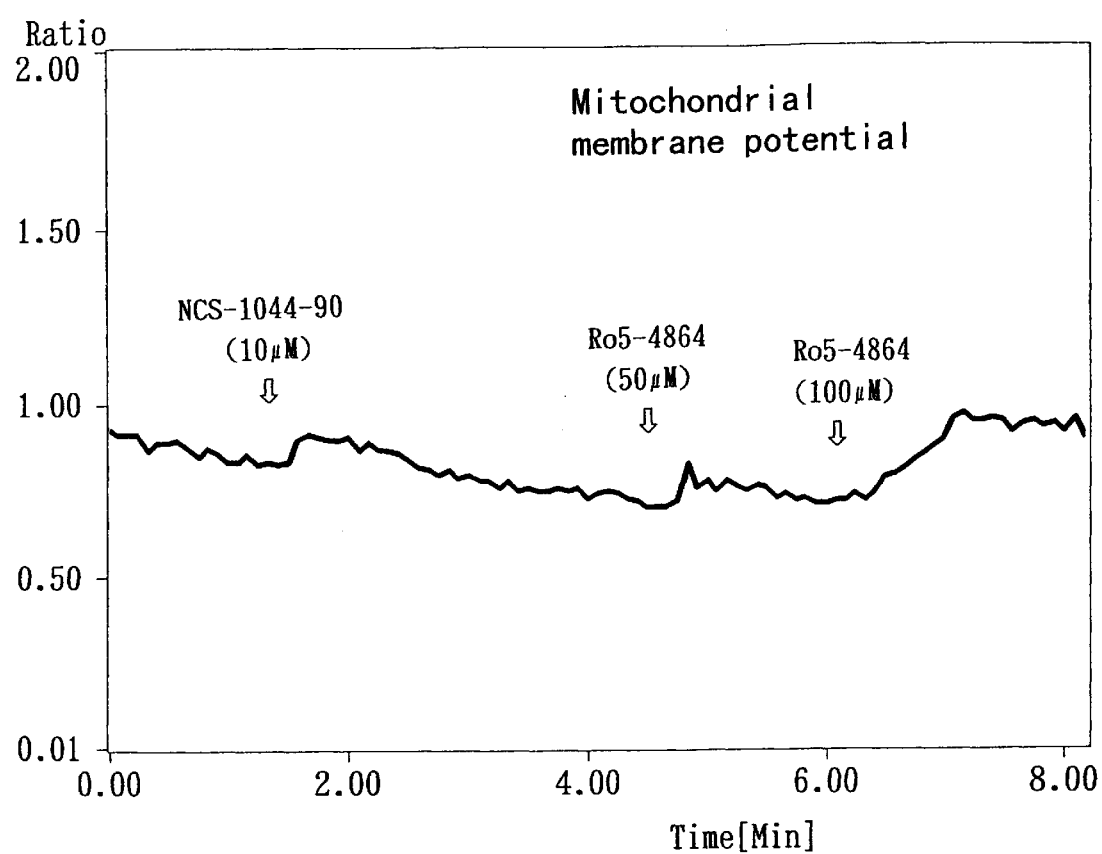
FIG. 10 shows an effect of Ro5-4864 on intracellular mitochondrial membrane potential in cells treated with NCS-1044-90.

Effect of Ro5-4864 on the Mitochondrial Membrane Potential in NCS-1044-90 Treated Cells No change in the intracellular mitochondrial membrane potential was observed by treatment with NCS-1044-90 (10 μM). When Ro5-4864 (50 μM) was added to cells treated with NCS-1044-90 (10 μM), only a very small elevation of the intracellular mitochondrial membrane potential was recognized. However, when the cells were further treated with Ro5-4864 (100 μM), a slight and gentle elevation of the membrane potential was observed (FIG. 10).

INDUSTRIAL APPLICABILITY

The medicament of the present invention has activities of stabilizing mitochondrial membranes, and preventing mitochondrial functional abnormality caused by unstabilization of mitochondrial membranes such as depolarization of mitochondrial membranes. The medicament is thus useful as an active ingredient of medicaments for prophylactic and/or preventive and/or therapeutic treatment of diseases caused by mitochondrial functional abnormality, or diseases with mitochondrial functional abnormality such as ischemic diseases or toxic diseases.

What is claimed is:

1. A prophylactic and/or therapeutic method for treating a disease caused by mitochondrial functional abnormality, or a disease with mitochondrial functional abnormality, comprising:

administering a prophylactically and/or therapeutically effective amount, to a patient in need of such treatment, of a medicament comprising as an active ingredient a substance having a stabilizing effect on mitochondrial membranes by suppressing or eliminating depolarization of mitochondrial membranes which is caused by elevation of intracellular calcium ion concentration;

wherein the disease comprises abnormality of mitochondrial enzyme activity, mitochondrial gene mutation disease, Parkinson's disease, amyotrophic lateral sclerosis (ALS), mitochondrial encephalomyopathy, Niemann-Pick's disease, renal failure, hepatic failure, or at least one of a gas poisoning, an alcoholic poisoning, a drug poisoning, a pesticide poisoning, a heavy metal poisoning, and a poisoning caused by a toxin of an animal or a plant.

2. The method of claim 1, wherein the disease comprises at least one of renal failure, and hepatic failure.

3. The method of claim 1, wherein the disease comprises at least one of a gas poisoning, an alcoholic poisoning, a drug poisoning, a pesticide poisoning, a heavy metal poisoning, and a poisoning caused by a toxin of an animal or a plant.

4. The method of claim 1, wherein the disease comprises at least one of abnormality of mitochondrial enzyme activity, mitochondrial gene mutation disease, Parkinson's disease, amyotrophic lateral sclerosis (ALS), mitochondrial encephalomyopathy, and Niemann-Pick's disease.

5. The method of claim 1, wherein the disease comprises elevation of intracellular calcium concentration.

6. The method of claim 1, wherein the medicament comprises as an active ingredient a compound represented by the following formula:

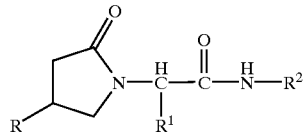

wherein R represents hydrogen atom or hydroxyl group, $R^1$ represents hydrogen atom or methyl group, and $R^2$ represents a pyridyl group or a phenyl group substituted with 1 to 3 substituents which may be the same or different, and the substituent on the phenyl group is one of a halogen atom, trifluoromethyl group, nitro group, acetyl group, a straight- or branched-alkyl group having 1–4 carbon atoms, a straight- or branched alkoxyl group having 1–4 carbon atoms, a straight- or branched-alkylmercapto group having 1–7 carbon atoms, a substituted alkylmercapto group represented by the general formula: —S—(CH$_2$)$_n$—CH($R^3$)($R^4$) wherein n represents 1 or 2, $R^3$ represents hydrogen atom or methyl group, and $R^4$ represents hydroxyl group, or an amino group represented by the general formula: —N($R^8$)($R^9$) wherein $R^8$ represents hydrogen atom or methyl group, and $R^9$ represents methyl group, benzyl group, or a substituted benzyl group, or $R^8$ and $R^9$ combine with each other to represent a substituted pyrrolidine ring together with the nitrogen atom in the formula, a sulphonyl group represented by the following general formula: —SO$_2R^5$ wherein $R^5$ represents amino group or an alkyl group having 1–3 carbon atoms, and an aminoethoxycarbonyl group represented by the formula: —COO(CH$_2$)$_2$—N($R^6$)($R^7$) wherein $R^6$ and $R^7$ independently represent hydrogen atom, methyl group, or ethyl group.

7. The method of claim 1, wherein the medicament comprises, as an active ingredient, one of the following compounds;

2-oxo-1-pyrrolidinylacetic acid 2,6-dimethylanilide;

4-hydroxy-2-oxo-1-pyrrolidinylacetic acid 2,6-diethylanilide;

4-hydroxy-2-oxo-1-pyrrolidinylacetic acid 2,6-dimethylanilide;

2-(2-oxo-pyrrolidinyl)propionic acid N-3-pyridinylamide;

2-oxo-1-pyrrolidinylacetic acid 4-isopropylmercaptoanilide;

2-(2-oxo-1-pyrrolidinyl)-1-propionic acid 4-(2-butylmercapto)-anilide;

2-(2-oxo-1-pyrrolidinyl)propionic acid 4-isopropylanilide;

2-(2-oxo-1-pyrrolidinyl)propionic acid 2,4-dimethylanilide;

2-(2-oxo-1-pyrrolidinyl)propionic acid 2,4,6-trimethylanilide;

2-(2-oxo-1-pyrrolidinyl)propionic acid 2-methoxy-5-methylanilide;

2-(2-oxo-1-pyrrolidinyl)propionic acid 2,6-dichloroanilide;

2-pyrrolidoneacetamide;

1-anisoyl-2-pyrrolidinone; and 4-hydroxy-2-oxo-1-pyrrolidineacetamide.

8. The method of claim 1, wherein the medicament comprises, as an active ingredient, one of 2-oxo-1-pyrrolidinylacetic acid 2,6-dimethylanilide, 2-pyrrolidoneacetamide, 1-anisoyl-2-pyrrolidinone, and 4-hydroxy-2-oxo-1-pyrrolidineacetamide.

9. The method of claim 1, wherein the medicament comprises 2-oxo-1-pyrrolidinylacetic acid 2,6-dimethylanilide as an active ingredient.

10. The method of claim 1, wherein the medicament comprises as an active ingredient a compound represented by the following formula:

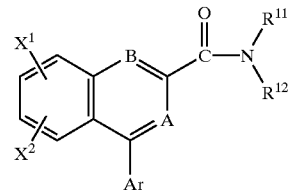

wherein $R^{11}$ and $R^{12}$ independently represent a straight- or branched-alkyl group having 1–6 carbon atoms, a cycloalkyl group having 3–7 carbon atoms, a phenylalkyl group whose alkyl moiety has 1–3 carbon atoms, or a cycloalkyl-substituted alkyl group, or represent an alkenyl group or an alkynyl group having 3–6 carbon atoms in which a double bond or a triple bond is not present at the 1–2 position relative to the nitrogen atom; A and B independently represent N or CH; $X^1$ and $X^2$ independently represent a halogen atom, a straight- or branched-alkyl group having 1–3 carbon atoms, a straight- or branched-alkoxyl group having 1–3 carbon atoms, nitro group, or trifluoromethyl group; Ar represents phenyl group, a pyridyl group, a thienyl group, or a substituted phenyl group in which the substituent on the phenyl group consists of 1 or 2 functional groups which are one of a halogen atom, a straight- or branched-alkyl group having 1–4 carbon atoms, a straight- or branched-alkoxyl group having 1–4 carbon atoms, a straight- or branched-alkylthio group having 1–4 carbon atoms, trifluoromethyl group, and nitro group.

11. The method of claim 10, wherein the medicament comprises, as an active ingredient, one of N-methyl-N-(1-methylpropyl)-(2-chlorophenyl)isoquinoline-3-carboxamide, N-methyl-N-(1-(S)-methylpropyl)-(2-chloropenyl)isoquinoline-3-carboxamide, and N-methyl-N-(1-(R-)-methylpropyl)-(2-chlorophenyl)isoquinoline-3-carboxamide.

12. The method of claim 1, wherein the medicament comprises as an active ingredient a compound represented by the following formula:

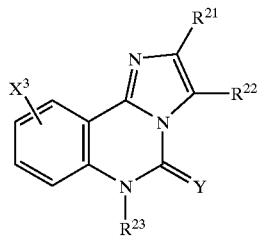

wherein $R^{21}$ represents unsubstituted phenyl group, a substituted phenyl group in which the substituent on the phenyl group consists of 1 or 2 substituents which are one of a halogen atom, a straight- or branched-alkyl group having 1–6 carbon atoms, and a straight- or branched-alkoxy group having 1–6 carbon atoms, or a thienyl group; $R^{22}$ represents hydrogen atom, a halogen atom, a straight- or branched-alkyl group having 1–6 carbon atoms, or a substituted straight- or branched-alkyl group having 1–6 carbon atoms in which the substituent is one of amino group, an alkylamino group, and a dialkylamino group; $R^{23}$ represents a group represented by the formula: $(R^{24})(R^{25})N-CO-Q-$ wherein Q represents a straight- or branched-alkylene group having 1–6 carbon atoms, and $R^{24}$ and $R^{25}$ independently represent a straight- or branched-alkyl group having 1–6 carbon atoms, unsubstituted phenyl group, or a substituted phenyl group in which the substituent on the phenyl group consists of 1 or 2 substituents which are one of a halogen atom, a straight- or branched-alkyl group having 1–6 carbon atoms, and a straight- or branched-alkoxyl group having 1–6 carbon atoms; $X^3$ represents hydrogen atom or a halogen atom; and Y represents oxygen atom or sulfur atom.

13. The method of claim 12, wherein the medicament comprises 2-(3-chlorophenyl)-3-bromo-6-(N-methyl-N-phenylacetamido)-5-oxo-5,6-dihydroimidazo(1,2-c)quinazoline as an active ingredient.

14. A prophylactic and/or therapeutic method for treating a disease caused by mitochondrial functional abnormality, or a disease with mitochondrial functional abnormality, comprising:
administering a prophylactically and/or therapeutically effective amount, to a patient in need of such treatment, of a medicament comprising as an active ingredient a substance having a stabilizing effect on mitochondrial membrane to maintain or restore ATP producing ability of mitochondria at a physiological level when intracellular calcium ion concentration is elevated;
wherein the disease comprises abnormality of mitochondrial enzyme activity, mitochondrial gene mutation disease, Parkinson's disease, amyotrophic lateral sclerosis (ALS), mitochondrial encephalomyopathy, Niemann-Pick's disease, renal failure, hepatic failure, or at least one of a gas poisoning, an alcoholic poisoning, a drug poisoning, a pesticide poisoning, a heavy metal poisoning, and a poisoning caused by a toxin of an animal or a plant.

15. A prophylactic and/or therapeutic method for treating a disease caused by mitochondrial functional abnormality, or a disease with mitochondrial functional abnormality, comprising:
administering a prophylactically and/or therapeutically effective amount, to a patient in need of such treatment, of a medicament for treatment of a disease caused by mitochondrial functional abnormality, or a disease with mitochondrial functional abnormality, which comprises an antagonist for the mitochondrial benzodiazepine receptor;
wherein the disease comprises abnormality of mitochondrial enzyme activity, mitochondrial gene mutation disease, Parkinson's disease, amyotrophic lateral sclerosis (ALS), mitochondrial encephalomyopathy, Niemann-Pick's disease, renal failure, hepatic failure, or at least one of a gas poisoning, an alcoholic poisoning, a drug poisoning, a pesticide poisoning, a heavy metal poisoning, and a poisoning caused by a toxin of an animal or a plant.

16. A prophylactic and/or therapeutic method for treating a disease caused by mitochondrial functional abnormality, or a disease with mitochondrial functional abnormality, comprising:
administering a prophylactically and/or therapeutically effective amount, to a patient in need of such treatment, of a mitochondrial membrane stabilizer comprising an antagonist for a mitochondria benzodiazepine receptor as an active ingredient;
wherein the disease comprises abnormality of mitochondrial enzyme activity, mitochondrial gene mutation disease, Parkinson's disease, amyotrophic lateral sclerosis (ALS), mitochondrial encephalomyopathy, Niemann-Pick's disease, renal failure, hepatic failure, or at least one of a gas poisoning, an alcoholic poisoning, a drug poisoning, a pesticide poisoning, a heavy metal poisoning, and a poisoning caused by a toxin of an animal or a plant.

17. A prophylactic and/or therapeutic method for treating a disease caused by mitochondrial functional abnormality, or a disease with mitochondrial functional abnormality, comprising:
administering a prophylactically and/or therapeutically effective amount, to a patient in need of such treatment, of a mitochondrial membrane potential stabilizer comprising an antagonist for a mitochondria benzodiazepine receptor as an active ingredient;
wherein the disease comprises abnormality of mitochondrial enzyme activity, mitochondrial gene mutation disease, Parkinson's disease, amyotrophic lateral sclerosis (ALS), mitochondrial encephalomyopathy, Niemann-Pick's disease, renal failure, hepatic failure, or at least one of a gas poisoning, an alcoholic poisoning, a drug poisoning, a pesticide poisoning, a heavy metal poisoning, and a poisoning caused by a toxin of an animal or a plant.

* * * * *

UNITED STATES PATENT AND TRADEMARK OFFICE
CERTIFICATE OF CORRECTION

PATENT NO.     : 6,417,220 B2
DATED          : July 9, 2002
INVENTOR(S)    : M. Yoshii et al.

It is certified that error appears in the above-identified patent and that said Letters Patent is hereby corrected as shown below:

<u>Column 17,</u>
Line 17, "(2-chloropenyl)" should be -- (2-chlorophenyl) --.

Signed and Sealed this

Fifteenth Day of April, 2003

JAMES E. ROGAN
*Director of the United States Patent and Trademark Office*